(12) United States Patent
Sage

(10) Patent No.: US 8,483,845 B2
(45) Date of Patent: Jul. 9, 2013

(54) ANCHOR FOR IMPLANTABLE MEDICAL DEVICE

(75) Inventor: Shahn S. Sage, Andover, MN (US)

(73) Assignee: Greatbatch Ltd., Clarence, NY (US)

( * ) Notice: Subject to any disclaimer, the term of this patent is extended or adjusted under 35 U.S.C. 154(b) by 355 days.

(21) Appl. No.: 13/045,874

(22) Filed: Mar. 11, 2011

(65) Prior Publication Data

US 2012/0232624 A1 Sep. 13, 2012

(51) Int. Cl.
*A61N 1/05* (2006.01)
(52) U.S. Cl.
CPC .................................... *A61N 1/0558* (2013.01)
USPC ........................... 607/117; 607/126; 607/130
(58) Field of Classification Search
USPC .......... 607/115–117, 126, 132, 149; 606/232; 604/174–175, 177
See application file for complete search history.

(56) References Cited

U.S. PATENT DOCUMENTS

| 5,376,108 | A | 12/1994 | Collins et al. |
| 5,814,021 | A | 9/1998 | Balbierz |
| 6,473,654 | B1 | 10/2002 | Chinn |
| 6,901,287 | B2 | 5/2005 | Davis et al. |
| 7,831,313 | B2 | 11/2010 | Lauro |
| 2007/0050005 | A1* | 3/2007 | Lauro ........................... 607/126 |
| 2007/0239242 | A1 | 10/2007 | Graubert |
| 2009/0248054 | A1 | 10/2009 | Sage et al. |
| 2010/0030311 | A1 | 2/2010 | Lazeroms et al. |
| 2010/0076487 | A1 | 3/2010 | Ilahi |
| 2012/0035692 | A1* | 2/2012 | Cantlon et al. ................. 607/116 |

FOREIGN PATENT DOCUMENTS

EP 0 865 799 A2 9/1998

* cited by examiner

*Primary Examiner* — Carl H Layno
*Assistant Examiner* — Jessica Sarcione
(74) *Attorney, Agent, or Firm* — Michael P. Horvath

(57) ABSTRACT

An anchor for an implantable medical device, anchor delivery tools, kits, and methods, all directed to securing a therapy delivery element at a target location in a patient. An anchor for a therapy delivery element having an outer surface about which the anchor is disposable. The anchor includes a body portion having elastomeric properties, a first opening, a second opening, and a non-linear lumen extending though the body portion from the first opening to the second opening in a relaxed state. The non-linear lumen becomes a linear lumen in a stretched state. The linear lumen of the body portion is adapted to receive the therapy delivery element and the non-linear lumen frictionally engages the outer surface of the therapy delivery element in the relaxed state.

16 Claims, 10 Drawing Sheets

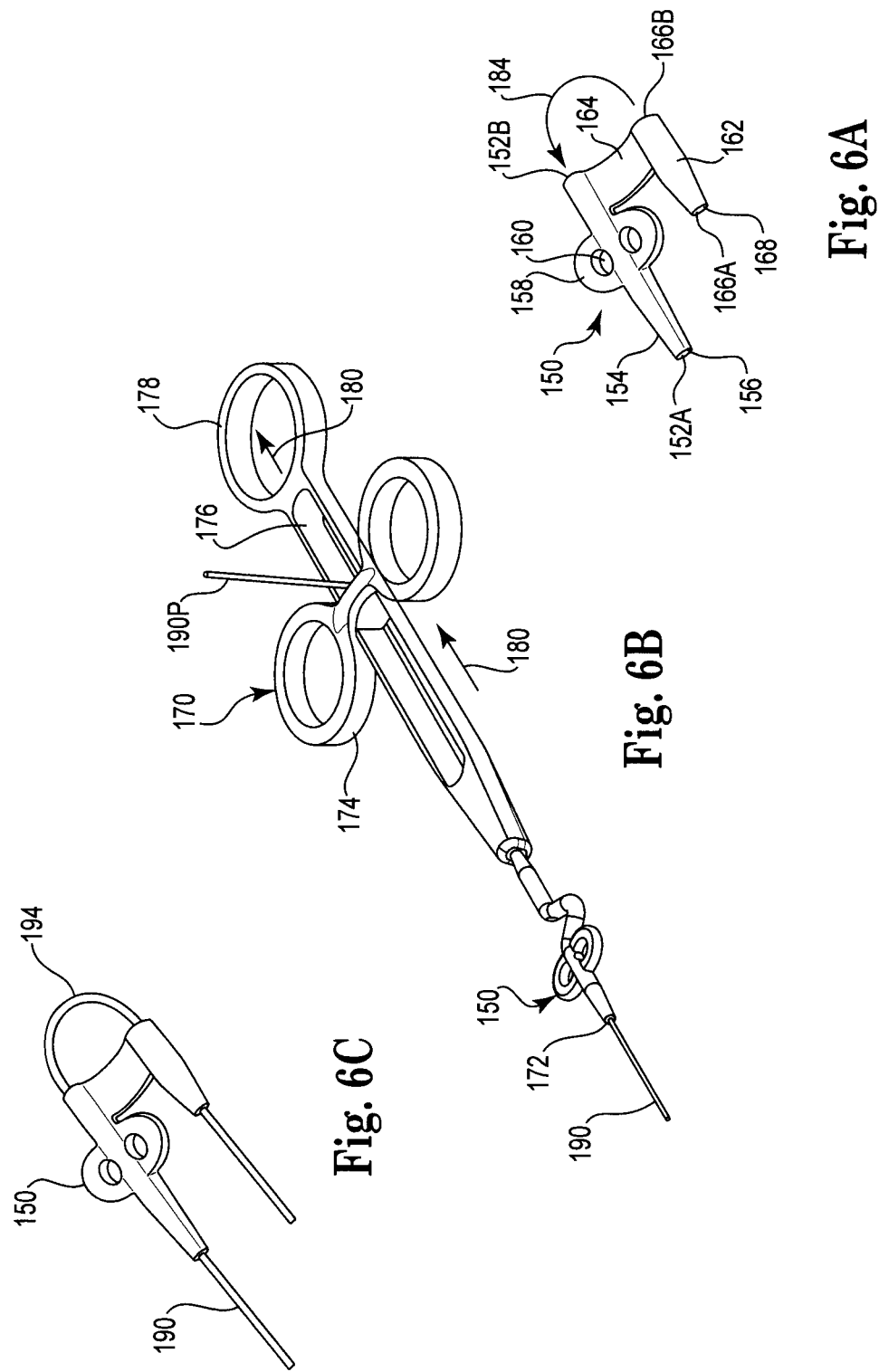

US 8,483,845 B2

ANCHOR FOR IMPLANTABLE MEDICAL DEVICE

FIELD

The present disclosure is directed to an anchor for an implantable medical device with increased holding force, and in particular, to elastomeric anchors with non-linear lumens that frictionally engage the outer surface of the therapy delivery element in a relaxed state. The increased holding force can be reduced or removed by applying tension to the anchor to straighten the non-linear lumen.

BACKGROUND

Implantable medical devices are used for a wide variety of medical conditions, such as for example, cardiac pace making, cardiac rhythm management, treatments for congestive heart failure, implanted defibrillators, and neurostimulation. Neurostimulation encompasses a wide range of applications, such as for example, pain control, nervous tremor mitigation, incontinent treatment, epilepsy seizure reduction, and vagus nerve stimulation for clinical depression.

These implantable medical devices generally include an implanted pulse generator that generates electrical pulses or signals that are transmitted to a targeted tissue or nerves through an implanted lead. Controlled placement of the implanted leads is required for improved therapeutic efficacy or reduced side effects. Retaining the implanted lead in the desired location also creates difficulties because the location may change in time as the patient moves.

U.S. Pat. Publication No. 2009/0248054 (Sage et al.) discloses a typical anchor that is placed about the implanted lead. The anchor is made from an elastic material that provides a radially compressive force around the implantable lead. The anchor is sutured to subcutaneous tissue of the patient to secure the lead relative to a target location.

Existing anchors suffer from a variety of shortcomings, including insufficient or excessive gripping of the lead, and damage to the implantable lead during suturing of the anchor to the patient.

BRIEF SUMMARY

The present disclosure is directed to an anchor for a therapy delivery element having an outer surface about which the anchor is disposable. The anchor includes a body portion having elastomeric properties, a first opening, a second opening, and a non-linear lumen extending though the body portion from the first opening to the second opening in a relaxed state. The non-linear lumen becomes a linear lumen in a stretched state. The linear lumen of the body portion is adapted to receive the therapy delivery element in the stretch state. The non-linear lumen of the relaxed state frictionally engages the outer surface of the therapy delivery element.

The therapy delivery element generally assumes a shape of the non-linear lumen in the relaxed state. In one embodiment, at least a portion of the therapy delivery element has a cross-sectional area greater than a cross-sectional area of the non-linear lumen in the relaxed state, such that the body portion compressively engages the therapy delivery element. The non-linear lumen can be one of serpentine, tortuous, curved, non-straight, or curvilinear.

In one embodiment, the body portion includes a first body portion having a first opening, a second opening, and a first lumen extending though the first body portion from the first opening to the second opening, and a second body portion having a first opening, a second opening, and a second lumen extending though the second body portion from the first opening to the second opening. A flexible tab attaches the first body portion to the second body portion, such that the first and second lumens are non-aligned in the relaxed state. The first and second lumens can be parallel or perpendicular with respect to each other in the relaxed state. The therapy delivery element generally assumes the alignment first and second lumens in the relaxed state.

The body portion optionally includes one or more annular ribs. At least one retention member with a suture hole is preferably attached to the anchor.

The present disclosure is also directed to an anchor system including the anchor discussed herein, and an anchor delivery tool. The anchor delivery tool includes an anchor delivery tube with a delivery lumen adapted to receive the therapy delivery element, and an outer surface with a cross-sectional area greater than a cross-sectional area of the linear lumen of the body portion in the stretch state, such that the linear lumen of the body portion compressively engages the delivery tube. The anchor delivery tube is adapted to retract into the anchor delivery tool to deploy the anchor onto the outer surface of the therapy delivery element.

The present disclosure is also directed to a kit with two or more anchors having different non-linear lumens, a therapy delivery element, and an anchor delivery tool.

The present disclosure is also directed to a method of delivering an anchor for an implantable medical device in a patient. The elastomeric body portion of the anchor is stretched to convert a relaxed non-linear lumen to a stretched linear lumen. An anchor delivery tube is inserted into the linear lumen. The linear lumen has a cross-sectional area less than a cross-sectional area of the delivery tube, such that the body portion compressively engages the delivery tube in a stretched state. A therapy delivery element is inserted into a lumen in the anchor delivery tube. The anchor delivery tube is positioned relative to the therapy delivery element where the anchor is to be located. The anchor delivery tube is retracted into an anchor delivery tool so that the anchor resumes a relaxed state and the non-linear lumen of the body portion frictionally engages the outer surface of the therapy delivery in the relaxed state. The anchor is sutured to the patient and the anchor delivery tube is removed from the therapy delivery element.

The therapy delivery element generally assumes a non-linear shape of the non-linear lumen when the body portion is in the relaxed state. The non-linear lumen optionally compressively engages the therapy delivery element in the relaxed state.

The present disclosure is also directed to a method of implanting a neurostimulation system within a living body. An implantable pulse generator is implanted within the living body. Electrodes at a distal end of a therapy delivery element are positioned at a target location within the living body. The present anchor is engaged with the therapy delivery element as discussed above. The proximal end of the therapy delivery element is electrically coupled to the implantable pulse generator.

BRIEF DESCRIPTION OF THE SEVERAL VIEWS OF THE DRAWING

FIG. 6A is a perspective view of an alternate anchor for an implantable medical device in accordance with an embodiment of the present disclosure.

FIG. 6B is a perspective view of a delivery device engaged with the anchor of FIG. 6A.

FIG. 6C is a perspective view of the anchor of FIG. 6A engaged with an implantable medical device.

DETAILED DESCRIPTION OF SOME EMBODIMENTS

The description that follows relates to a spinal cord stimulation (SCS) system. However, it is to be understood that the while the present disclosure lends itself well to applications in SCS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

In another embodiment, one or more of the therapy delivery elements may be a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be an electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, extensions for any of the above, or combinations thereof. "Target tissue site" refers generally to the target site for implantation of a therapy delivery element, regardless of the type of therapy.

Figure 1A:
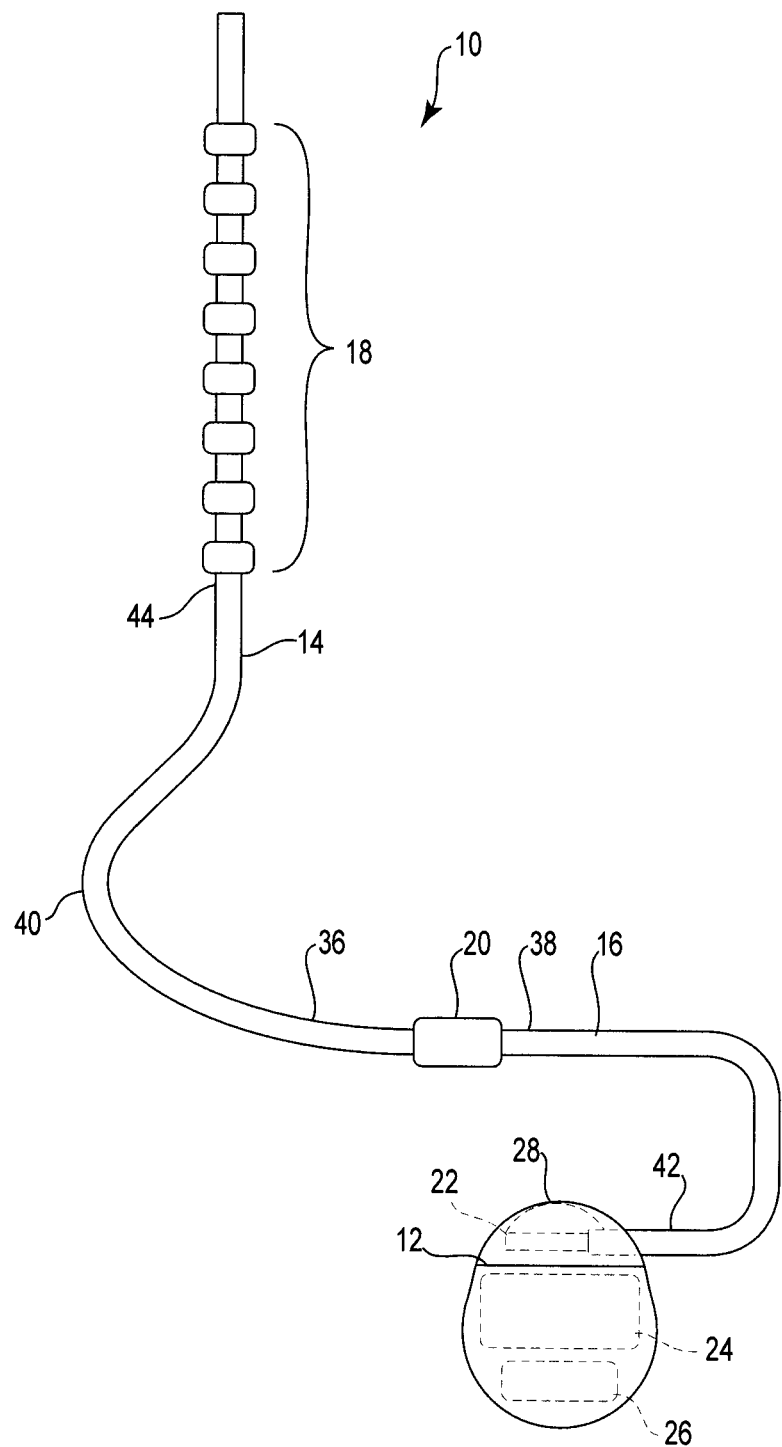
FIG. 1A is a schematic illustration of a therapy delivery system.

FIG. 1A illustrates a generalized therapy delivery system 10 that may be used in spinal cord stimulation (SCS), as well as other stimulation applications. The therapy delivery system 10 generally includes an implantable pulse generator 12, an implantable therapy delivery element 14, which carries an array of electrodes 18 (shown exaggerated for purposes of illustration), and an optional implantable extension lead 16. Although only one therapy delivery element 14 is shown, typically two or more therapy delivery elements 14 are used with the therapy delivery system 10 (See e.g., FIG. 1C).

The therapy delivery element 14 includes elongated body 40 having a proximal end 36 and a distal end 44. The elongated body 40 typically has a diameter of between about 0.03 inches to 0.07 inches and a length within the range of 30 cm to 90 cm for spinal cord stimulation applications. The elongated body 40 may be composed of a suitable electrically insulative material, such as, a polymer (e.g., polyurethane or silicone), and may be extruded from as a uni-body construction.

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector assembly 22 associated with housing 28. Alternatively, the proximal end 36 of the therapy delivery element 14 can be electrically coupled directly to the connector 20.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 is protected from the body tissue and fluids. The connector assembly 22 is disposed in a portion of the housing 28 that is, at least initially, not sealed. The connector assembly 22 carries a plurality of contacts that electrically couple with respective terminals at proximal ends of the therapy delivery element 14 or extension lead 16. Electrical conductors extend from the connector assembly 22 and connect to the electronic subassembly 24.

Figure 1B:
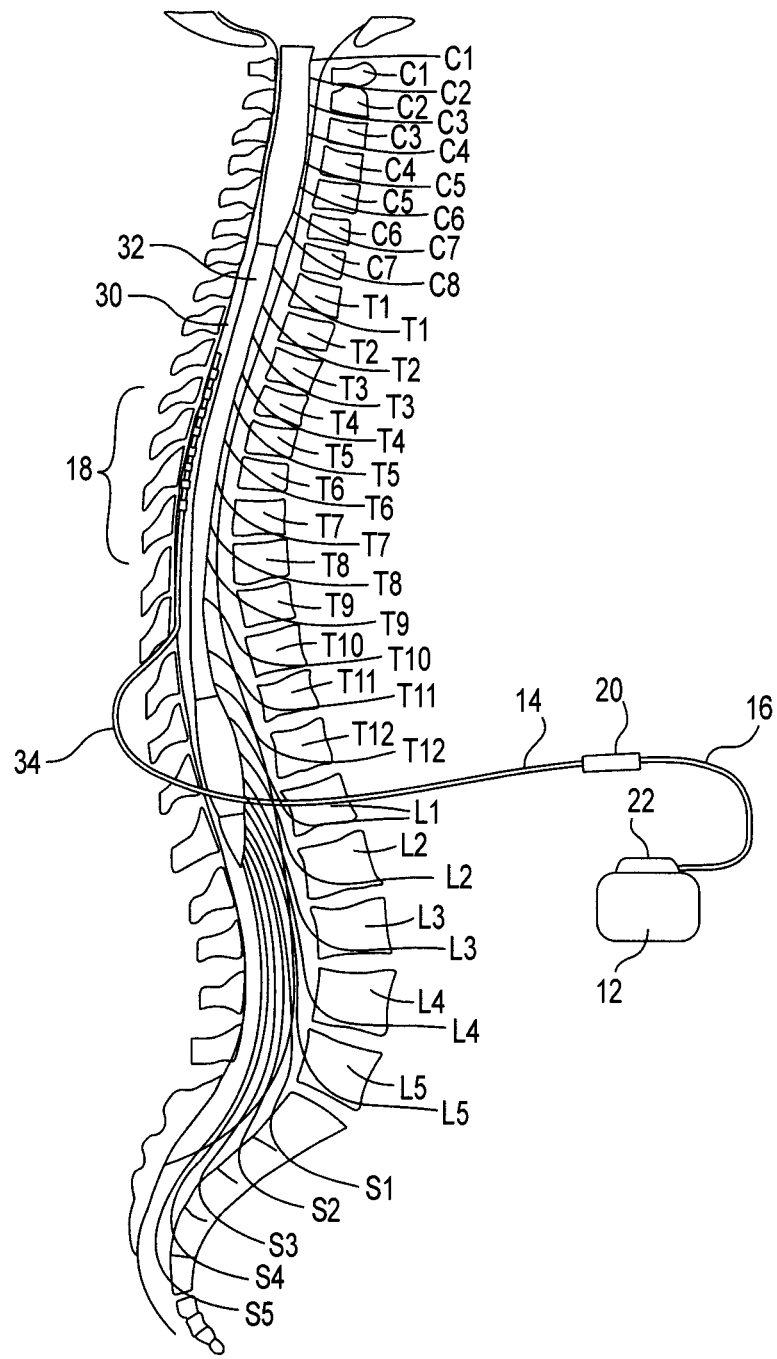
FIG. 1B is a schematic illustration of an environment for a therapy delivery system in accordance with an embodiment of the present disclosure.

FIG. 1B illustrates the therapy delivery element 14 implanted in the epidural space 30 of a patient in close proximity to the dura, the outer layer that surrounds the spinal cord 32, to deliver the intended therapeutic effects of spinal cord electrical stimulation. The target stimulation sites may be anywhere along the spinal cord 32, such as for example proximate the sacral nerves.

Figure 1C:
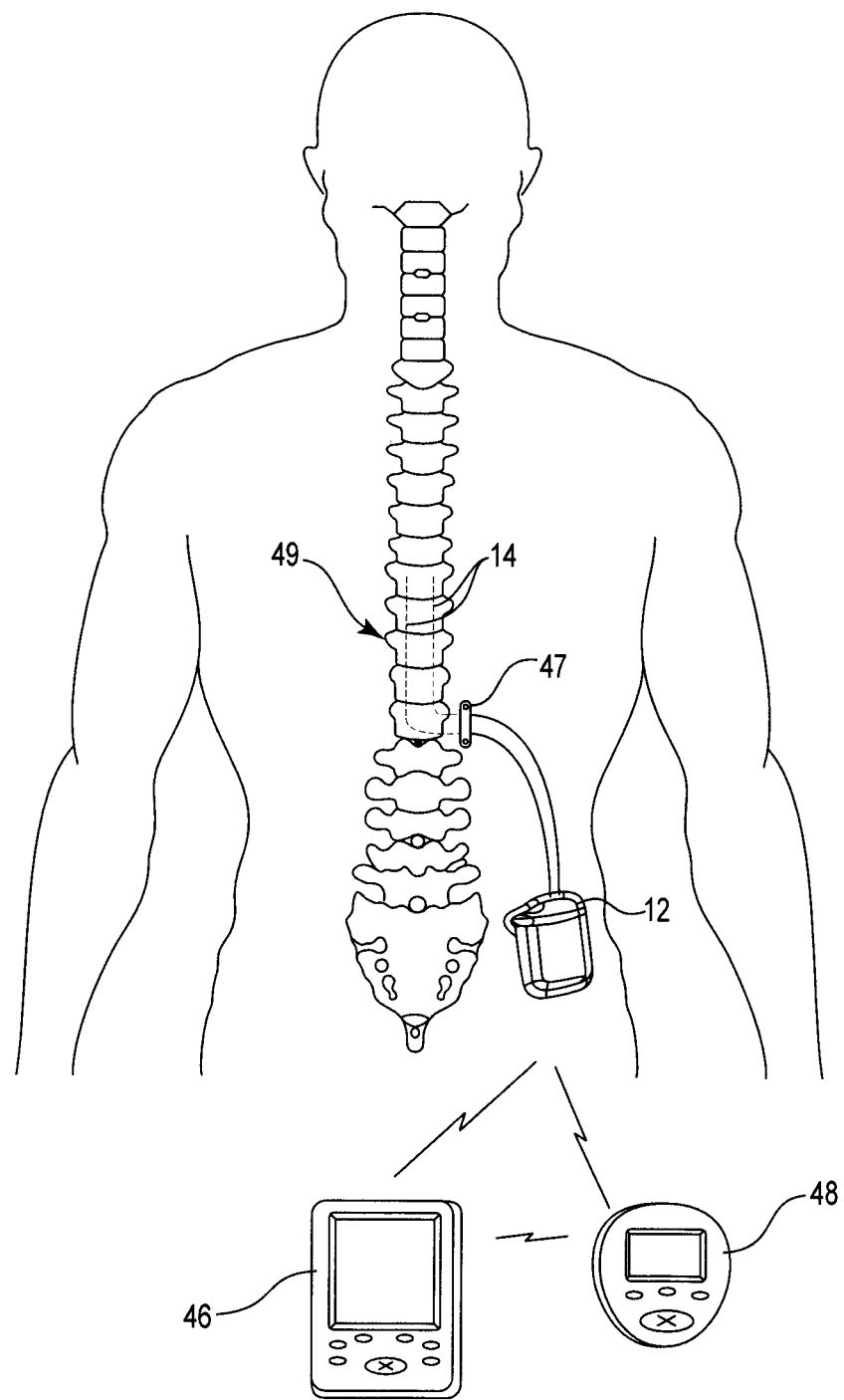
FIG. 1C is an alternate illustration of the environment for an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 1C. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector assembly 22 of the implantable pulse generator 12, since different manufacturers use different connectors at the ends of their stimulation leads and are not always compatible with the connector assembly 22.

As illustrated in FIG. 1C, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 48, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Since the implantable pulse generator 12 is located remotely from target location 49 for therapy, the therapy delivery element 14 and/or the extension leads 16 is typically routed through a pathways subcutaneously formed along the torso of the patient to a subcutaneous pocket where the implantable pulse generator 12 is located. Anchor 47 is used to secure the therapy delivery elements 14 in the epidural space 30. As used hereinafter, "lead" and "lead extension" are used interchangeably, unless content clearly dictates otherwise.

Figure 2:
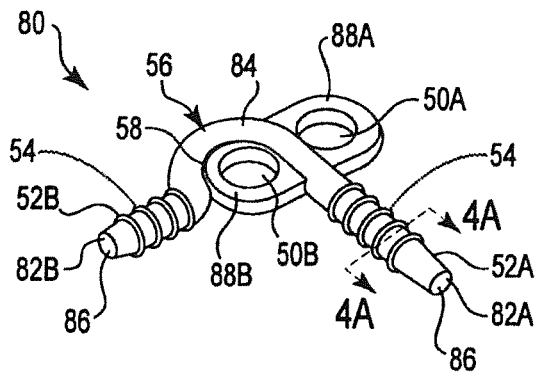
FIG. 2 is a perspective view of an anchor for an implantable medical device in accordance with an embodiment of the present disclosure.

FIG. 2 is a perspective view of an alternate anchor 80 in accordance with an embodiment of the present disclosure. The anchor 80 includes first and second openings 82A, 82B ("82") in body portion 84 that are fluidly connected by lumen 86. Retention members 88A, 88B ("88") attached to body portion 84 include suture holes 50A, 50B ("50") for suturing the anchor 80 to the patient. In the illustrated embodiment, distal ends 52A, 52B ("52") of the body portion 84 include annular reinforcing ribs 54 that increase the radial compression generated by the anchor 80, as discussed below. The lumen 86 may have a square, circular, oval, rectangular, or any other cross-sectional shape.

The lumen 86 follows a non-linear path 56. As used herein, "non-linear" refers to a conduit or lumen that follows a serpentine, tortuous, curved, non-straight, or curvilinear path. In the embodiment of FIG. 2, the lumen 86 includes curved portion 58 and the distal end 52A is oriented generally perpendicular to distal end 52B.

At least part of the body portion 84 is formed of elastomeric material. In the preferred embodiment, the entire anchor 80, including the retention members 88 are molded from the same elastomeric material. Alternatively, the retention members 88 may be a first material and the body portion 84 a second material. In one embodiment, the retention members 88 and the body portion 84 are molded separately and attached during a post-processing step, such as by an adhesive, ultrasonic welding, solvent welding, mechanical interlock, and the like. The anchor 80 may include any number of retention members 88 and suture holes 50. Alternatively, the retention members 88 may include tissue engaging structures, such as for example, barbs, tines, or the like.

The body portion 84 may be formed from any suitable elastic material, such as for example, copolymers of styrene-butadiene, polybutadiene, polymers formed from ethylene-propylene diene monomers, polychloroprene, polyisoprene, copolymers of acrylonitrile and butadiene, copolymers of isobutyldiene and isoprene, polyurethanes and the like. The body portion 44 is preferably formed of material capable of being stretched up to about 50% or more without substantial loss of structural integrity. For example, body portion 44 may be capable of being stretched up to about 75% or more, 100% or more, 150% or more, or 200% or more. Silicone is an example of an elastic material that is generally expandable up to about 100% or more without substantial loss of structural integrity.

Figure 3:
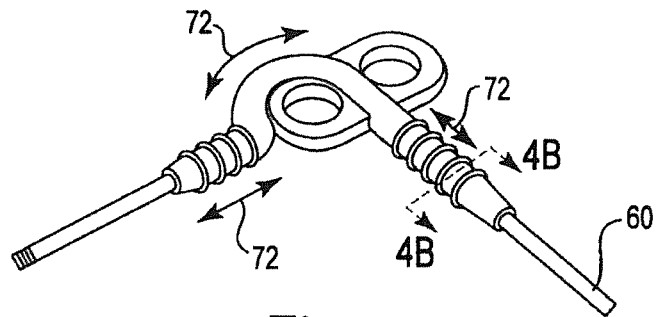
FIG. 3 is a perspective view of the anchor of FIG. 1 engaged with an implantable therapy delivery element in accordance with an embodiment of the present disclosure.

FIG. 3 illustrates the anchor 80 engaged with implantable therapy delivery element 60. The flexible therapy delivery element 60 generally follows the non-linear path 58 of the lumen 86.

Figures 4A, 4B:
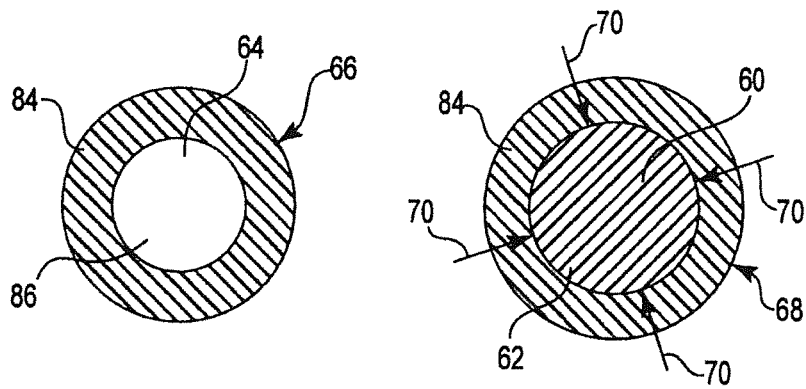
FIG. 4A is a cross-sectional view of the anchor of FIG. 2.
FIG. 4B is a cross-sectional view of the anchor and implantable therapy delivery element of FIG. 3.

In the relaxed state 66 illustrated in FIG. 4A, the lumen 86 has a cross-sectional area 64 that is less than the cross-sectional area 62 of the flexible therapy delivery element 60. In order for the anchor 80 to fit over the therapy delivery element 60, at least a portion of the body portion 84 is stretched radially from the relaxed state 66 to the stretch state 68 illustrated in FIG. 4B. In the stretch state 68, the body portion 84 applies compressive force 70 radially inward and normal to the surface of the therapy delivery element 60.

The ribs 54 increase the compressive force 70 at the distal ends 52 of the anchor 80. Therefore, in the illustrated embodiment, the compressive force 70 is not uniform along the length of the body portion 84. The ribs 54 also facility gripping of the anchor 80 by the surgeon, such as if it is necessary to reposition the therapy delivery element 60 within the anchor 80.

As used herein, a "stretched state" refers to elastic deformation, without compromising structural integrity. A structurally uncompromised body portion will generally be free of cracks or tears or will be capable of returning to substantially its relaxed state (i.e. to an inner diameter prior to radial stretching).

The therapy delivery element 60 is retained relative to the anchor 80 by a combination of the compressive force 70 and friction forces 72 created by, and generally parallel to, the non-linear path 58. Since the anchor 80 is made from an elastomeric material, the surgeon can manually straighten the body portion 84 to reduce these frictional forces 72 to permit repositioning of the therapy delivery element 60 relative to the anchor 80. In addition to the frictional forces 72, the non-linear path 56 provides strain relief to the system.

The forces 70, 72 are preferably sufficient to prevent the therapy delivery element 60 from moving relative to the anchor 80 under typical forces experienced when the anchor 80 is sutured to a patient. In various embodiments, a pull force of about 1 foot-pound force (0.45 kilogram-force) to about 5 foot-pounds force (2.3 kilogram-force) is preferred.

Figure 5A:
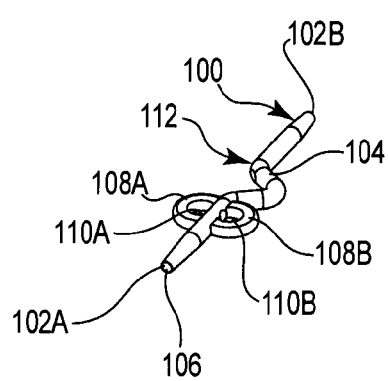
FIG. 5A is a perspective view of an alternate anchor for an implantable medical device in accordance with an embodiment of the present disclosure.

FIG. 5A is a perspective view of an alternate anchor 100 in accordance with an embodiment of the present disclosure. The anchor 100 includes first and second openings 102A, 102B ("102") in body portion 104 that are fluidly connected by lumen 106. A pair of retention members 108A, 108B ("108") attached to body portion 104 include suture holes 110A, 110B ("100") for suturing the anchor 100 to the patient. The lumen 106 includes non-linear path 112 through which a therapy delivery element 114 (see FIG. 5D), such as a lead or catheter, can be inserted and attached to the patient.

Figure 5B:
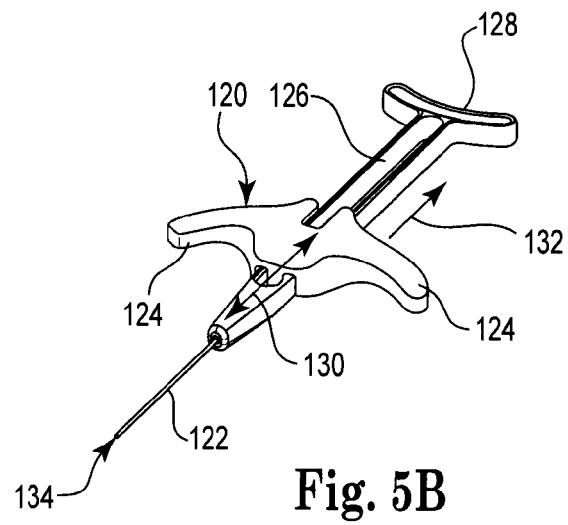
FIG. 5B is a perspective view of a delivery device in accordance with an embodiment of the present disclosure.

FIG. 5B illustrates anchor delivery tool 120 in accordance with an embodiment of the present disclosure. Delivery tube 122 is attached to finger grip 124, both of which slide in recess 126 of handle 128 along axis 130. As the finger grip 124 is pulled in direction 132, the delivery tube 122 moves in the same direction 132 and is withdrawn into recess 126 of handle 128. The delivery tube 122 may be formed of high durometer material, such as for example, stainless steel, titanium, polycarbonate, polypropylene, or the like. In one embodiment, the delivery tube 122 is coated with a material to reduce friction, such ethylene tetrafluoroethylene (ETFE) or polytetrafluoroethylene (PTFE).

Figure 5C:
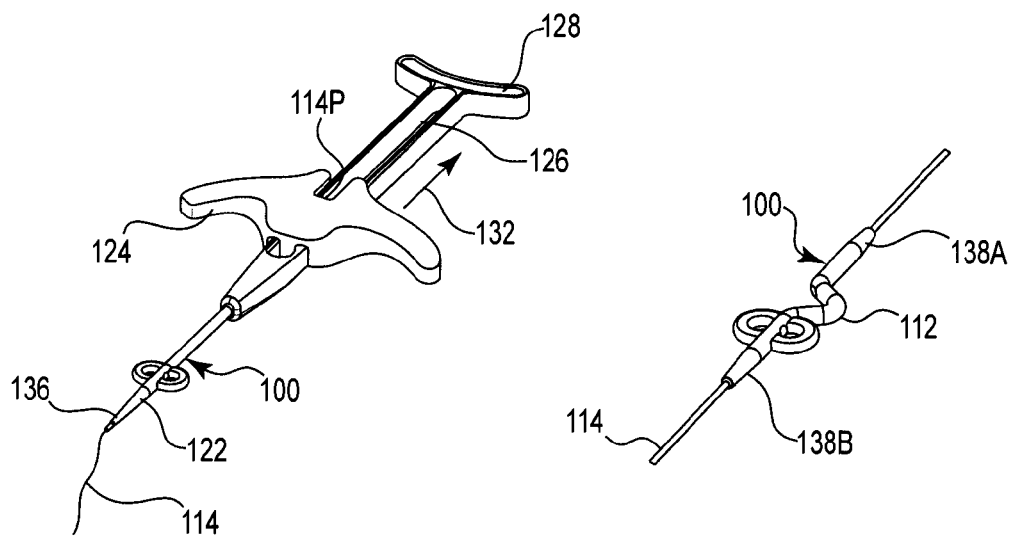
FIG. 5C is a perspective view of the delivery device of FIG. 5B engaged with the anchor of FIG. 5A.

FIG. 5C illustrates the delivery tube 122 inserted through the lumen 106 of the anchor 100. The elastomeric material of the anchor 100 permits the non-linear path 112 to be straightened on the rigid or semi-rigid delivery tube 122. The delivery tube 122 preferably has an outside diameter greater than the inside diameter of the lumen 106 so as to retain the anchor 100 on the delivery tube.

The delivery tube 122 preferably has delivery lumen 134 with a diameter sized to receive element 114. In the illustrated embodiment, the element 114 is inserted in the delivery lumen 134 of the delivery tube 122. The delivery lumen 134 preferably extends to the recess 126 of the handle 128, so that proximal end 114P of the element 114 extends out through the recess.

The surgeon advances the anchor delivery tool 120 along the length of the element 114 until the anchor 100 is in the desired location within the patient. In the preferred embodiment, the surgeon sutures the anchor 100 to the patient before releasing the anchor 100 from the anchor delivery tool 120. As a result, the rigid delivery tube 122 protects the element 114 from punctures or other damage during suturing. After suturing, the surgeon pulls the finger grip 124 in the direction 132 so as to retract the delivery tube 122 into the recess 126. The anchor 100 slides off the end 136 of the delivery tube 122 onto the element 114.

Figure 5D:
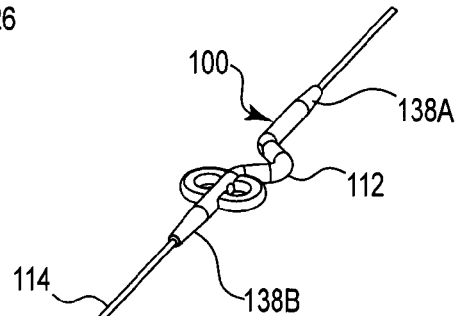
FIG. 5D is a perspective view of the anchor of FIG. 5A engaged with an implantable medical device.

As discussed in detail above, the lumen 106 of the anchor 100 has a cross-sectional area less than the cross sectional area of the therapy delivery element 114, resulting in a compressive engagement of the element 114 by the anchor 100. As best illustrated in FIG. 5D, the elastomeric material of the anchor 100 resumes substantially its original shape, including the non-linear path 112. The element 114 assumes the shape 112 of the lumen 106. The non-linear path 112 of the lumen 106 increases the holding force between the element 114 and the anchor 100. This additional holding force can be reduces or eliminated by grasping the ends 138A 138B of the anchor 100 and pulling in the opposite direction to straighten the non-linear path 112.

FIG. 6A is a perspective view of an alternate anchor 150 in accordance with an embodiment of the present disclosure. The anchor 150 includes first and second openings 152A, 152B ("152") in first body portion 154 that are fluidly connected by lumen 156. A pair of retention members 158 attached to the first body portion 154 each includes suture holes 160 for suturing the anchor 150 to the patient. Second body portion 162 is attached to the first body portion 154 by flexible tab 164. The second body portion 162 also includes first and second openings 166A, 166B ("166") fluidly connected by lumen 168.

FIG. 6B illustrates anchor delivery tool 170 in accordance with an embodiment of the present disclosure. Delivery tube 172 is attached to finger grip 174, both of which slide in recess 176 of handle 178 in direction 180. As the finger grip 174 is pulled in direction 180, the delivery tube 172 moves in the same direction 180 and is withdrawn into recess 176 of handle 128.

In order to position the anchor 150 on the delivery tube 172, the second body portion 162 is rotated in direction 184 so that lumens 168 and 156 are generally co-linear. The delivery tube 172 is inserted into the opening 166A and through the lumen 168, then into the opening 152B and through the lumen 156, and finally out through the opening 152A.

As discussed above, the therapy delivery element 190 is inserted through the opening 172 of the delivery tube 172 so that the proximal end 192P extends out through the recess 176. The surgeon advances the anchor delivery tool 170 along the length of the therapy delivery element 190 until the anchor 150 is at the desired location within the patient. The surgeon then pulls the finger grip 174 in the direction 180 so as to retract the delivery tube 172 into the recess 176.

As illustrated in FIG. 6C, the anchor 150 slides off the end of the delivery tube 172 onto the therapy delivery element 190. The elastomeric material of the tab 164 causes the second body portion 162 to resumes substantially its original position. The therapy delivery element 190 assumes the shape 194 between the openings 152B and 166B. The non-linear path of the shape 194 increases the holding force between the therapy delivery element 190 and the anchor 150. This additional holding force can be reduces or eliminated by rotating the second body portion 162 in the direction 184 so that the lumens 156, 168 are generally co-linear.

Figure 7:
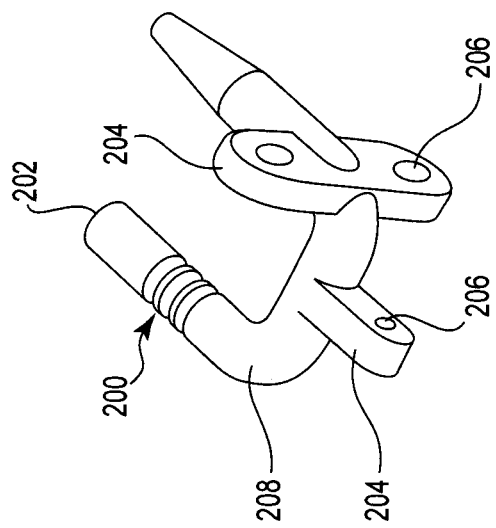
FIG. 7 is a perspective view of an alternate anchor for an implantable medical device in accordance with an embodiment of the present disclosure.

FIG. 7 is a perspective view of a U-shaped anchor 200 with a U-shaped lumen 202 for an implantable medical device in accordance with an embodiment of the present disclosure. Retention members 204 with suture holes 206 are attached at various locations along the body portion 208.

Figure 8:
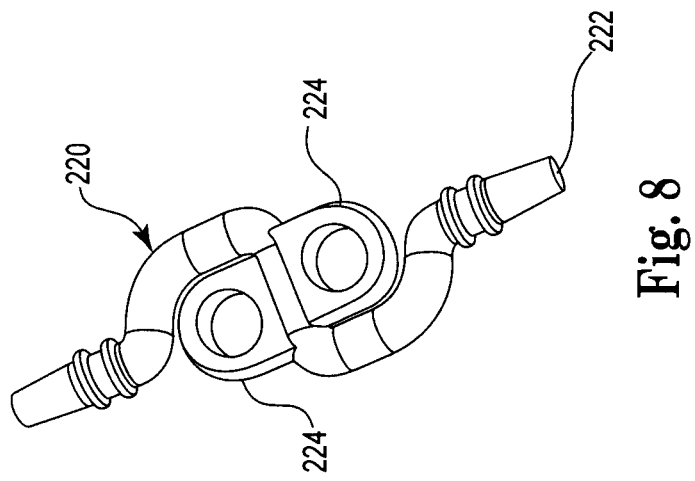
FIG. 8 is a perspective view of an alternate anchor for an implantable medical device in accordance with an embodiment of the present disclosure.

FIG. 8 is a perspective view of an alternate anchor 220 with an S-shaped lumen 222 for an implantable medical device in accordance with an embodiment of the present disclosure. Retention members 224 are arranged generally co-planar with the plane of the lumen 222.

Figure 9A:
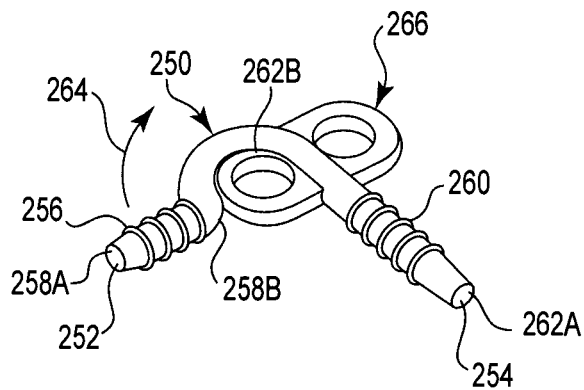
FIG. 9A is a perspective view of an alternate anchor in accordance with an embodiment of the present disclosure.
Figure 9B:
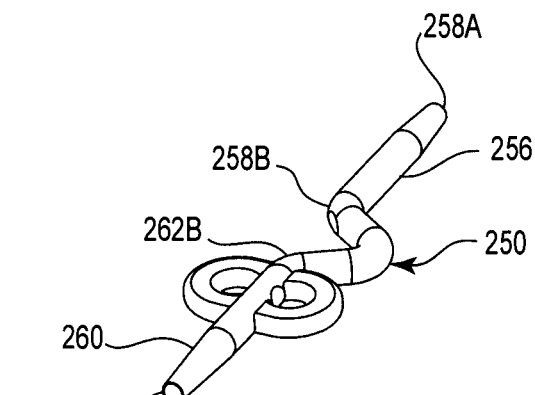
FIG. 9B is a perspective view of the anchor of FIG. 9A with aligned lumens in accordance with an embodiment of the present disclosure.

FIGS. 9A and 9B illustrate an alternate anchor 250 with two non-aligned lumens 252, 254 in accordance with an embodiment of the present disclosure. The anchor 250 includes first body portion 256 with first and second openings 258A, 258B ("258") fluidly connected by lumen 252, and second body portion 260 with first and second openings 262A, 262B ("262") fluidly coupled by lumen 254. In relaxed configuration 266 illustrated in FIG. 9A, the lumens 252, 254 are generally perpendicular.

Figure 10:
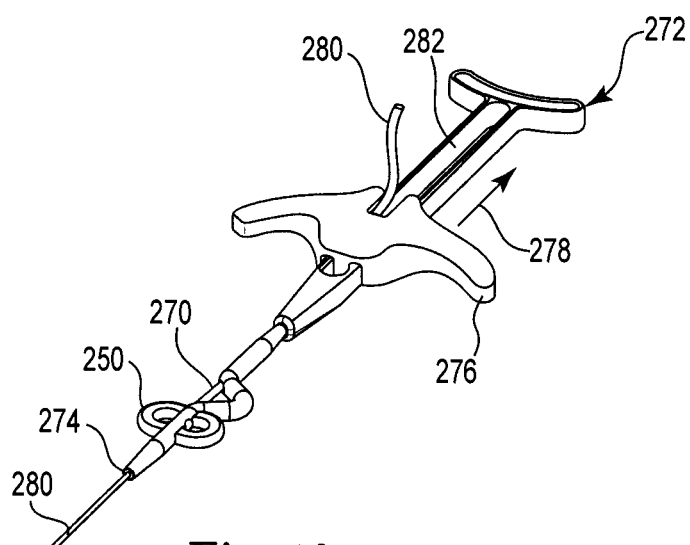
FIG. 10 is a perspective view of an anchor delivery tool with the anchor of FIG. 9A in accordance with an embodiment of the present disclosure.

FIG. 9B illustrates the body portion 256 rotated in direction 264 to align the lumens 252, 254 to facilitate insertion of delivery tube 270 of the anchor delivery tool 272, as illustrated in FIG. 10. As discussed above, the therapy delivery element 280 is then inserted through the opening 274 of the delivery tube 270. The surgeon pulls the finger grip 276 in the direction 278 so as to retract the delivery tube 270 into the recess 282, resulting in the anchor 250 compressively engaging the therapy delivery element 280.

Figure 11A:
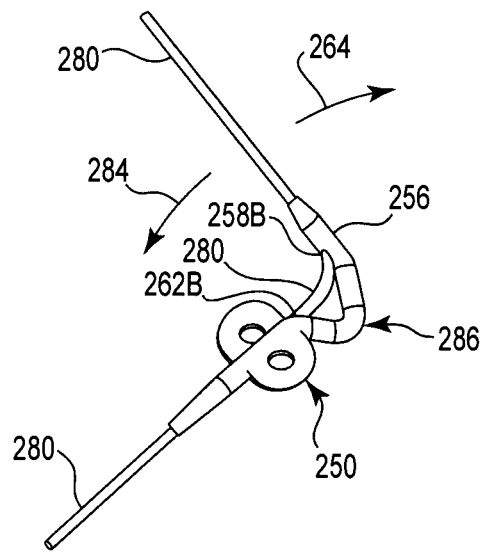
FIGS. 11A and 11B are perspective views of the anchor of FIG. 9A engaged with a therapy delivery element in accordance with an embodiment of the present disclosure.
Figure 11B:
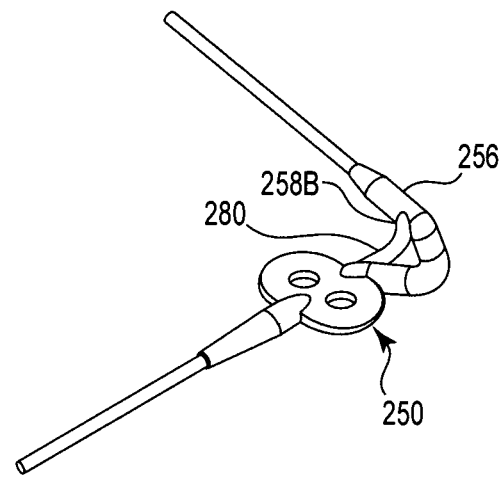

FIGS. 11A and 11B illustrate the anchor 250 deployed on the therapy delivery element 280. The elastomeric properties of the anchor 250 causes the body portion 256 to partially rotate in direction 284. The column strength of the therapy delivery element 280 between the openings 262B and 258B prevents full rotation of the body portion 256 back to the relaxed configuration 266 illustrated in FIG. 9A.

The therapy delivery element 280 assumes the shape 286 of the anchor. The non-linear path of the shape 286 increases the holding force between the therapy delivery element 280 and the anchor 250. This additional holding force can be reduces or eliminated by rotating the body portion 256 in the direction 264 so that the lumens 252, 254 are generally co-linear.

Figure 12:
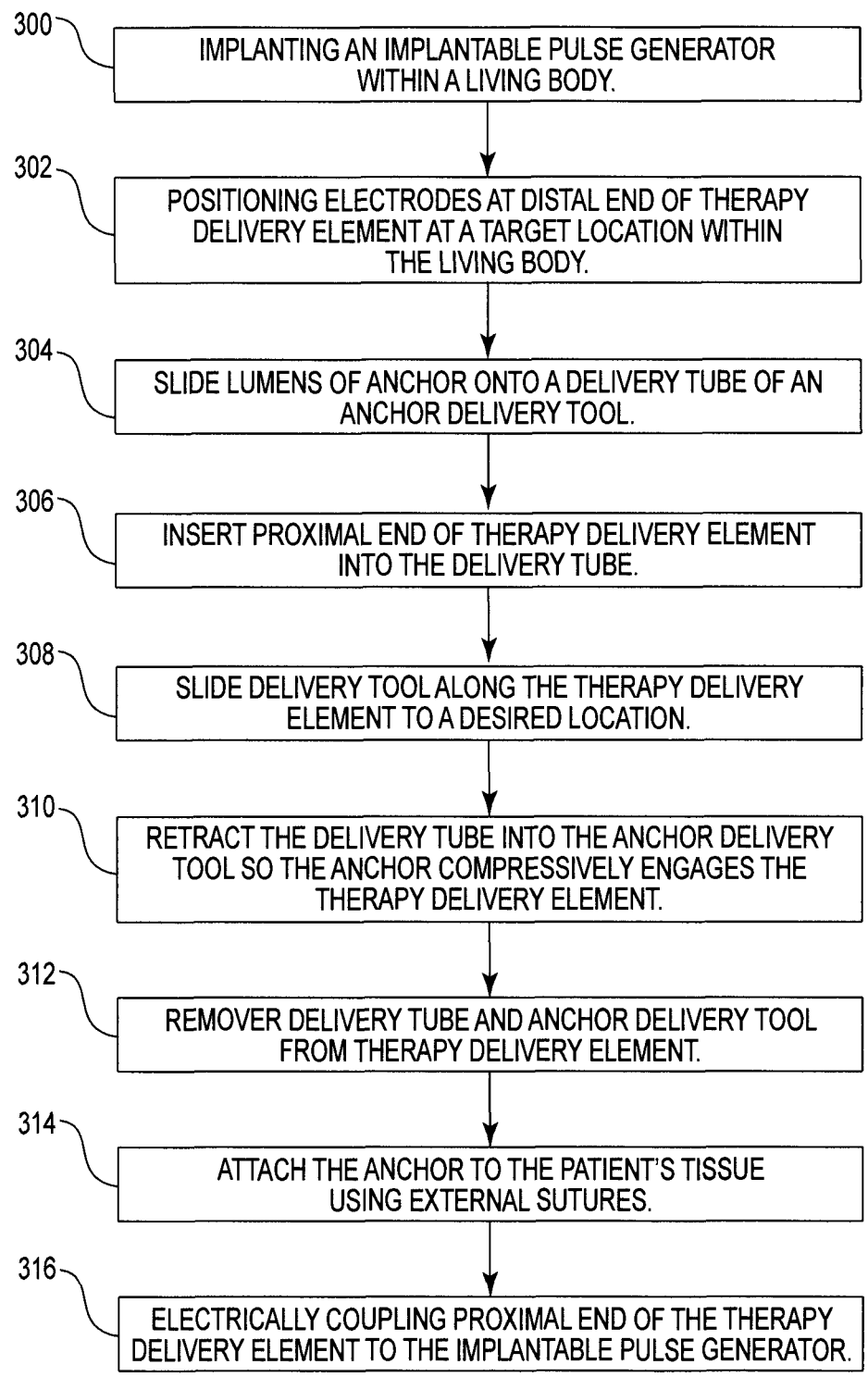
FIG. 12 is a flow diagram of a method of implanting a neurostimulation system within a living body in accordance with an embodiment of the present disclosure.

FIG. 12 is a flow diagram of a method of implanting a neurostimulation system within a living body in accordance with an embodiment of the present disclosure. The method includes the steps of implanting an implantable pulse generator within the living body (300). Electrodes at a distal end of a therapy delivery element are positioned at a target location within the living body (302). The lumen(s) of the anchor are slid onto the delivery tube of the anchor delivery device (304). A proximal end of the therapy delivery element is inserted into the delivery tube (306). The delivery tube is slid along the therapy delivery element to a desired location (308). The surgeon then retracts the delivery tube into the anchor delivery tool so the anchor compressively engages the therapy delivery element (310). The delivery tube and the anchor delivery tool are slid off of the proximal end of the therapy delivery element (312). The surgeon then attaches the anchor to the patient's tissue, such as for example, using staples or sutures (314). Finally, the proximal end of the therapy delivery element is electrically coupled to the implantable pulse generator (316).

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. An anchor for a therapy delivery element having an outer surface about which the anchor is disposable, the anchor comprising:
a body portion having elastomeric properties comprising a first opening, a second opening, and a non-linear lumen extending though the body portion from the first opening to the second opening in a relaxed state, and a linear lumen in a stretched state, wherein the linear lumen of the body portion is adapted to receive the therapy delivery element in the stretch state, and the non-linear lumen of the body portion frictionally engages the outer surface of the therapy delivery element in the relaxed state.

2. The anchor of claim 1 wherein the therapy delivery element generally assumes a shape of the non-linear lumen in the relaxed state.

3. The anchor of claim 1 wherein at least a portion of the therapy delivery element has a cross-sectional area greater than a cross-sectional area of the non-linear lumen in the relaxed state, such that the body portion compressively engages the therapy delivery element.

4. The anchor of claim 1 wherein the non-linear lumen comprises one of serpentine, tortuous, curved, non-straight, or curvilinear.

5. The anchor of claim 1 wherein the body portion comprises:
a first body portion having a first opening, a second opening, and a first lumen extending though the first body portion from the first opening to the second opening;
a second body portion having a first opening, a second opening, and a second lumen extending though the second body portion from the first opening to the second opening; and
a flexible tab attaching the first body portion to the second body portion such that the first and second lumens are non-aligned in the relaxed state.

6. The anchor of claim 5 wherein the first and second lumens are one of parallel or perpendicular with respect to each other in the relaxed state.

7. The anchor of claim 5 wherein the therapy delivery element generally assumes the alignment first and second lumens in the relaxed state.

8. The anchor system of claim 1 wherein the body portion comprises one or more annular ribs.

9. The anchor of claim 1 comprising at least one retention member with a suture hole attached to the anchor.

10. An anchor system comprising:
an anchor of claim 1; and
an anchor delivery tool comprising an anchor delivery tube with a delivery lumen adapted to receive the therapy delivery element, and an outer surface with a cross-sectional area greater than a cross-sectional area of the linear lumen of the body portion in the stretch state, such that the linear lumen of the body portion compressively engages the delivery tube.

11. The anchor system of claim 10 wherein the anchor delivery tube is adapted to retract into the anchor delivery tool to deploy the anchor onto the outer surface of the therapy delivery element.

12. A kit comprising:
a first anchor comprising a body portion having elastomeric properties, the body portion comprising a first opening, a second opening, and a first non-linear lumen extending though the body portion from the first opening to the second opening in a relaxed state, and a first linear lumen in a stretched state, wherein the first linear lumen of the body portion is adapted to receive a therapy delivery element and the first non-linear lumen of the body portion frictionally engages an outer surface of the therapy delivery in the relaxed state;
a second anchor comprising a body portion having elastomeric properties, the body portion comprising a first opening, a second opening, and a second non-linear lumen extending though the body portion from the first opening to the second opening in a relaxed state, and a second linear lumen in a stretched state, wherein the second linear lumen of the body portion is adapted to receive the therapy delivery element and the second non-linear lumen of the body portion frictionally engages the outer surface of the therapy delivery in the relaxed state, wherein the first non-linear lumen comprises a configuration different than the second non-linear lumen;
a therapy delivery element having an outer surface about which the body portion of the first or second anchors is disposable; and
an anchor delivery tool comprising an anchor delivery tube with a delivery lumen adapted to receive the therapy delivery element, and an outer surface with a cross-sectional area greater than a cross-sectional area of the first and second linear lumens of the body portions in the stretch state, such that the body portions compressively engage the delivery tube.

13. A method of delivering an anchor for an implantable medical device in a patient, the method comprising the steps of:
stretching an elastomeric body portion of an anchor to convert a relaxed non-linear lumen to a stretched linear lumen;
inserting an anchor delivery tube into the linear lumen, the linear lumen having a cross-sectional area less than a cross-sectional area of the delivery tube, such that the body portion compressively engages the delivery tube in a stretched state;
inserting a therapy delivery element into a lumen in the anchor delivery tube;
positioning the anchor delivery tube relative to the therapy delivery element where the anchor is to be located;
retracting the anchor delivery tube into an anchor delivery tool so that the anchor resumes a relaxed state and the non-linear lumen of the body portion frictionally engages the outer surface of the therapy delivery in the relaxed state;
suturing the anchor to the patient; and
removing the anchor delivery tube from the therapy delivery element.

14. The method of claim 13 comprising the therapy delivery element generally assuming a non-linear shape of the non-linear lumen when the body portion is in the relaxed state.

15. The method of claim 13 comprising the non-linear lumen compressively engaging the therapy delivery element in the relaxed state.

16. A method of implanting a neurostimulation system within a living body, the method comprising the steps of:
implanting an implantable pulse generator within the living body;
positioning electrodes at a distal end of a therapy delivery element at a target location within the living body;

stretching a non-linear lumen extending through an elastomeric body portion of an anchor to insert an anchor delivery tube, the non-linear lumen having a cross-sectional area less than a cross-sectional area of the delivery tube, such that the body portion compressively engages the delivery tube in a stretched state;

inserting a therapy delivery element into a lumen in the anchor delivery tube;

positioning the anchor delivery tube relative to the therapy delivery element where the anchor is to be located;

retracting the anchor delivery tube into an anchor delivery tool so that the anchor resumes a relaxed state and the non-linear lumen of the body portion frictionally engages the outer surface of the therapy delivery in the relaxed state;

suturing the anchor to the patient; and removing the anchor delivery tube from the therapy delivery element; and electrically coupling the proximal end of the therapy delivery element to the implantable pulse generator.

* * * * *

UNITED STATES PATENT AND TRADEMARK OFFICE
CERTIFICATE OF CORRECTION

PATENT NO.           : 8,483,845 B2                                                 Page 1 of 1
APPLICATION NO.      : 13/045874
DATED                : July 9, 2013
INVENTOR(S)          : Shahn S. Sage It is certified that error appears in the above-identified patent and that said Letters Patent is hereby corrected as shown below:

Title Page item (57) Abstract delete "though" and insert --through--

In the Specification

Column 1, line 49 delete "though" and insert --through--

Column 1, line 66 delete "though" and insert --through--

Column 2, line 2 delete "though" and insert --through--

In the Claims

Column 11, line 12 (Claim 1, line 6) delete "though" and insert --through--

Column 11, line 29 (Claim 4, line 3) after the word "curvilinear" insert --shape--

Column 11, line 33 (Claim 5, line 4) delete "though" and insert --through--

Column 11, line 36 (Claim 5, line 7) delete "though" and insert --through--

Column 12, line 2 (Claim 12, line 5) delete "though" and insert --through--

Column 12, line 12 (Claim 12, line 15) delete "though" and insert --through--

Signed and Sealed this
Thirtieth Day of September, 2014

Michelle K. Lee
*Deputy Director of the United States Patent and Trademark Office*